(12) United States Patent
Frey et al.

(10) Patent No.: US 10,758,283 B2
(45) Date of Patent: Sep. 1, 2020

(54) FIXATION DEVICES HAVING FENESTRATIONS AND METHODS FOR USING THE SAME

(71) Applicant: Mighty Oak Medical, Inc., Englewood, CO (US)

(72) Inventors: George Frey, Englewood, CO (US); Gregory Kana, Golden, CO (US)

(73) Assignee: MIGHTY OAK MEDICAL, INC., Englewood, CO (US)

( * ) Notice: Subject to any disclaimer, the term of this patent is extended or adjusted under 35 U.S.C. 154(b) by 523 days.

(21) Appl. No.: 15/675,104

(22) Filed: Aug. 11, 2017

(65) Prior Publication Data
US 2018/0042646 A1 Feb. 15, 2018

Related U.S. Application Data

(63) Continuation-in-part of application No. 15/416,975, filed on Jan. 26, 2017, now Pat. No. 9,987,024.
(Continued)

(51) Int. Cl.
*A61B 17/86* (2006.01)
*A61B 17/70* (2006.01)

(52) U.S. Cl.
CPC ...... *A61B 17/8625* (2013.01); *A61B 17/7032* (2013.01); *A61B 17/864* (2013.01); *A61B 17/866* (2013.01); *A61B 2017/8655* (2013.01)

(58) Field of Classification Search
CPC ............ A61B 17/7032; A61B 17/7034; A61B 17/7035; A61B 17/7037; A61B 17/7038;
(Continued)

(56) References Cited

U.S. PATENT DOCUMENTS 3,151,392 A 10/1967 Chambers
5,092,866 A 3/1992 Breard et al.
(Continued)

FOREIGN PATENT DOCUMENTS

CA 2736525 3/2010
CA 2862341 8/2013
(Continued)

OTHER PUBLICATIONS

"Calculator for Designing Compression Springs," eFunda, Inc., first published online Sep. 25, 2000 per Wayback Machine, 2 pages,[retrieved from: http://www.efunda.com/designstandards/springs/calc_comp_designer.cfm].
(Continued)

*Primary Examiner* — Eric S Gibson
(74) *Attorney, Agent, or Firm* — Fisherbroyles, LLP; Ian R. Walsworth (57) ABSTRACT

The present disclosure includes fixation devices, such as an orthopedic screw or implant, that comprises one or more porous elements or fenestrations to aid in osteo-integration of the fixation device. The fixation device may be additively manufactured using biocompatible materials such that the solid and porous aspects of the screw are fused together into a single construct. In yet another aspect, the fixation device comprises at least a portion or section incorporating a porous structure, which enables bony ingrowth through the porous section/portion of the screw, and thereby facilitates biocompatibility and improve mechanical characteristics. Methods for using the fixation device are also described herein.

20 Claims, 5 Drawing Sheets

Related U.S. Application Data (60) Provisional application No. 62/373,855, filed on Aug. 11, 2016.

(58) Field of Classification Search
CPC ... A61B 17/86; A61B 17/8605; A61B 17/861; A61B 17/8615; A61B 17/862; A61B 17/8625; A61B 17/863; A61B 17/8635; A61B 17/864; A61B 17/8645; A61B 17/8655; A61B 17/866
See application file for complete search history.

(56) References Cited

U.S. PATENT DOCUMENTS

| | | | |
|---|---|---|---|
| 5,129,904 A | | 7/1992 | Illi |
| 5,201,734 A | | 4/1993 | Cozard et al. |
| 5,291,901 A | | 3/1994 | Graf |
| 5,334,204 A | * | 8/1994 | Clewett ............. A61B 17/8625 606/312 |
| 5,360,448 A | | 11/1994 | Thramann |
| 5,387,213 A | | 1/1995 | Breard et al. |
| D359,557 S | | 6/1995 | Hayes |
| 5,490,409 A | | 2/1996 | Weber |
| 5,527,312 A | | 6/1996 | Ray |
| 5,562,737 A | | 10/1996 | Graf |
| 5,569,246 A | | 10/1996 | Ojima et al. |
| 5,591,233 A | | 1/1997 | Kelman et al. |
| 5,725,581 A | * | 3/1998 | Brånemark ......... A61F 2/30749 606/304 |
| D403,066 S | | 12/1998 | DeFonzo |
| 5,865,846 A | | 2/1999 | Bryan et al. |
| RE36,221 E | | 6/1999 | Breard et al. |
| D412,032 S | | 7/1999 | Mikula-Curtis et al. |
| 5,961,516 A | | 10/1999 | Graf |
| 5,993,453 A | | 11/1999 | Bullara et al. |
| 6,006,581 A | | 12/1999 | Holmes |
| D420,132 S | | 2/2000 | Bucholz et al. |
| 6,030,401 A | | 2/2000 | Marino |
| 6,035,691 A | | 3/2000 | Lin et al. |
| 6,048,343 A | * | 4/2000 | Mathis ............... A61B 17/7098 606/304 |
| 6,063,088 A | | 5/2000 | Winslow |
| D428,989 S | | 8/2000 | Segemark et al. |
| 6,113,602 A | | 9/2000 | Sand |
| 6,142,998 A | | 11/2000 | Smith et al. |
| 6,221,077 B1 | | 4/2001 | Rinner et al. |
| 6,290,724 B1 | | 9/2001 | Marino |
| 6,309,395 B1 | | 10/2001 | Smith et al. |
| 6,328,738 B1 | | 12/2001 | Suddaby |
| 6,364,880 B1 | | 4/2002 | Michelson |
| 6,402,750 B1 | | 6/2002 | Atkinson et al. |
| 6,445,211 B1 | | 9/2002 | Saripella |
| 6,565,572 B2 | * | 5/2003 | Chappius ........... A61B 17/3472 600/300 |
| 6,644,087 B1 | | 11/2003 | Ralph et al. |
| 6,663,633 B1 | | 12/2003 | Pierson, III |
| 6,711,432 B1 | | 3/2004 | Krause et al. |
| 6,719,795 B1 | | 4/2004 | Cornwall et al. |
| 6,755,839 B2 | | 6/2004 | Van Hoeck et al. |
| 6,835,207 B2 | | 12/2004 | Zacouto et al. |
| 6,863,671 B1 | * | 3/2005 | Strobel ................ A61F 2/0811 606/314 |
| 7,014,640 B2 | | 3/2006 | Kemppanien et al. |
| 7,025,769 B1 | | 4/2006 | Ferree |
| 7,066,957 B2 | | 6/2006 | Graf |
| 7,077,864 B2 | | 7/2006 | Bryd, III et al. |
| D532,515 S | | 11/2006 | Buttler et al. |
| D533,664 S | | 12/2006 | Butler et al. |
| 7,207,992 B2 | | 4/2007 | Ritland |
| 7,235,076 B2 | | 6/2007 | Pacheco |
| 7,261,716 B2 | * | 8/2007 | Strobel ............. A61B 17/8615 606/232 |
| 7,288,093 B2 | | 10/2007 | Michelson |
| 7,291,150 B2 | | 11/2007 | Graf |
| 7,341,590 B2 | | 3/2008 | Ferree |
| 7,387,643 B2 | | 6/2008 | Michelson |
| 7,406,775 B2 | | 8/2008 | Funk et al. |
| 7,454,939 B2 | | 11/2008 | Garner et al. |
| 7,491,180 B2 | | 2/2009 | Pacheco |
| 7,537,664 B2 | | 5/2009 | Oneill et al. |
| 7,559,931 B2 | | 7/2009 | Stone |
| 7,578,851 B2 | | 8/2009 | Dong et al. |
| 7,623,902 B2 | | 11/2009 | Pacheco |
| D606,195 S | | 12/2009 | Eisen et al. |
| 7,658,610 B2 | | 2/2010 | Knopp |
| D618,796 S | | 6/2010 | Cantu et al. |
| 7,844,356 B2 | | 11/2010 | Matov et al. |
| 7,854,752 B2 | | 12/2010 | Colleran et al. |
| 7,955,355 B2 | | 6/2011 | Cin |
| 7,957,824 B2 | | 6/2011 | Boronvinskih et al. |
| 7,957,831 B2 | | 6/2011 | Isaacs |
| 7,967,868 B2 | | 6/2011 | White et al. |
| 8,057,482 B2 | | 11/2011 | Stone et al. |
| 8,070,752 B2 | | 12/2011 | Metzger et al. |
| 8,092,465 B2 | | 1/2012 | Metzger et al. |
| 8,118,815 B2 | | 2/2012 | van der Walt |
| 8,159,753 B2 | | 4/2012 | Ojeda et al. |
| 8,167,884 B2 | | 5/2012 | Pacheco |
| 8,175,683 B2 | | 5/2012 | Roose |
| 8,206,396 B2 | | 6/2012 | Trabish |
| 8,214,014 B2 | | 7/2012 | Pacheco |
| 8,236,006 B2 | | 8/2012 | Hamada |
| 8,241,293 B2 | | 8/2012 | Stone et al. |
| 8,257,083 B2 | | 9/2012 | Berckmans et al. |
| D669,176 S | | 10/2012 | Frey |
| D669,984 S | | 10/2012 | Cheney et al. |
| 8,277,461 B2 | | 10/2012 | Pacheco |
| 8,282,646 B2 | | 10/2012 | Schoenefeld et al. |
| 8,292,967 B2 | | 10/2012 | Brown et al. |
| 8,298,235 B2 | | 10/2012 | Grinberg et al. |
| 8,298,237 B2 | | 10/2012 | Schoenefeld et al. |
| 8,298,242 B2 | | 10/2012 | Justis et al. |
| D672,038 S | | 12/2012 | Frey |
| 8,323,322 B2 | | 12/2012 | Dawson et al. |
| 8,357,111 B2 | | 1/2013 | Caillouette et al. |
| 8,377,066 B2 | | 2/2013 | Katrana et al. |
| 8,407,067 B2 | | 3/2013 | Uthgenannt et al. |
| 8,419,740 B2 | | 4/2013 | Aram et al. |
| D685,087 S | | 6/2013 | Voic |
| 8,460,303 B2 | | 6/2013 | Park |
| 8,475,505 B2 | * | 7/2013 | Nebosky ............. A61B 17/7061 606/304 |
| 8,480,679 B2 | | 7/2013 | Park et al. |
| 8,535,387 B2 | | 9/2013 | Meridew et al. |
| 8,540,719 B2 | | 9/2013 | Peukert et al. |
| 8,545,509 B2 | | 10/2013 | Park et al. |
| 8,549,888 B2 | | 10/2013 | Isaacs |
| 8,568,487 B2 | | 10/2013 | Witt et al. |
| 8,574,273 B2 | * | 11/2013 | Russell ............. A61B 17/0401 606/304 |
| 8,591,516 B2 | | 11/2013 | Metzger et al. |
| 8,603,180 B2 | | 12/2013 | White et al. |
| 8,607,603 B2 | | 12/2013 | Justis et al. |
| 8,608,748 B2 | | 12/2013 | Metzger et al. |
| 8,608,749 B2 | | 12/2013 | Meridew et al. |
| 8,632,547 B2 | | 1/2014 | Maxson et al. |
| 8,668,700 B2 | | 3/2014 | Catanzarite |
| 8,671,572 B2 | | 3/2014 | Schlottig et al. |
| D705,929 S | | 5/2014 | Frey |
| 8,721,651 B2 | | 5/2014 | Loke et al. |
| 8,758,357 B2 | | 6/2014 | Frey |
| 8,808,302 B2 | | 8/2014 | Roose et al. |
| 8,808,303 B2 | | 8/2014 | Stemniski et al. |
| 8,821,506 B2 | | 9/2014 | Mitchell |
| 8,858,561 B2 | | 10/2014 | White et al. |
| 8,864,769 B2 | | 10/2014 | Stone et al. |
| 8,870,889 B2 | | 10/2014 | Frey |
| D718,862 S | | 12/2014 | Matheny |
| D718,863 S | | 12/2014 | Matheny |
| D718,864 S | | 12/2014 | Matheny |
| 8,900,279 B2 | * | 12/2014 | Assell ............. A61B 17/8625 606/304 |

(56) References Cited

U.S. PATENT DOCUMENTS

| | | | |
|---|---|---|---|
| 8,945,193 B2* | 2/2015 | Kirschman | A61B 17/7064 606/304 |
| 8,979,749 B2 | 3/2015 | Gorek et al. | |
| 8,979,911 B2* | 3/2015 | Martineau | A61B 17/863 419/2 |
| 8,992,538 B2 | 3/2015 | Keefer | |
| D726,914 S | 4/2015 | Matheny | |
| 9,017,412 B2 | 4/2015 | Wolters et al. | |
| 9,044,285 B2 | 6/2015 | Harper | |
| 9,066,727 B2 | 6/2015 | Catanzarite et al. | |
| 9,066,816 B2 | 6/2015 | Allard et al. | |
| 9,113,971 B2 | 8/2015 | Metzger et al. | |
| D738,498 S | 9/2015 | Frey et al. | |
| 9,138,325 B2 | 9/2015 | Mouw | |
| 9,173,661 B2 | 11/2015 | Metzger et al. | |
| 9,173,692 B1* | 11/2015 | Kaloostian | A61B 17/8685 |
| D745,671 S | 12/2015 | Frey et al. | |
| D745,672 S | 12/2015 | Frey et al. | |
| D745,673 S | 12/2015 | Frey et al. | |
| 9,198,678 B2 | 12/2015 | Frey et al. | |
| 9,198,702 B2* | 12/2015 | Biedermann | A61B 17/8625 |
| 9,216,045 B2* | 12/2015 | Martineau | A61B 17/863 |
| 9,265,540 B2* | 2/2016 | Kirschman | A61B 17/863 |
| 9,445,852 B2* | 9/2016 | Sweeney | A61B 17/8836 |
| 9,451,973 B2 | 9/2016 | Heilman et al. | |
| 9,456,901 B2 | 10/2016 | Jones et al. | |
| D775,335 S | 12/2016 | Frey et al. | |
| 9,642,633 B2 | 5/2017 | Frey et al. | |
| 9,649,160 B2 | 5/2017 | van der Walt et al. | |
| 9,662,157 B2 | 5/2017 | Schneider et al. | |
| 9,675,400 B2 | 6/2017 | Katrana et al. | |
| 9,737,339 B2 | 8/2017 | Copp et al. | |
| 9,814,497 B1 | 11/2017 | Al-Habib et al. | |
| 9,826,991 B2 | 11/2017 | Kaiser et al. | |
| 9,827,028 B2* | 11/2017 | Biedermann | A61B 17/8625 |
| 9,839,448 B2 | 12/2017 | Reckling et al. | |
| 9,848,922 B2 | 12/2017 | Tohmeh et al. | |
| 9,913,669 B1 | 3/2018 | Scholl et al. | |
| 9,949,843 B2 | 4/2018 | Reiley et al. | |
| 9,968,408 B1 | 5/2018 | Casey et al. | |
| 9,987,024 B2 | 6/2018 | Frey et al. | |
| 10,085,784 B2 | 10/2018 | Ono et al. | |
| 10,166,033 B2 | 1/2019 | Reiley et al. | |
| 2004/0097925 A1 | 5/2004 | Boehm et al. | |
| 2004/0144149 A1 | 7/2004 | Strippgen et al. | |
| 2004/0147929 A1* | 7/2004 | Biedermann | A61B 17/7001 606/266 |
| 2004/0225292 A1* | 11/2004 | Sasso | A61B 17/8615 606/916 |
| 2004/0243481 A1 | 12/2004 | Bradbury et al. | |
| 2004/0267260 A1 | 12/2004 | Mack et al. | |
| 2005/0085815 A1 | 4/2005 | Harms et al. | |
| 2005/0148843 A1 | 7/2005 | Roose | |
| 2005/0177156 A1 | 8/2005 | Timm et al. | |
| 2005/0203514 A1 | 9/2005 | Jahng et al. | |
| 2005/0203519 A1 | 9/2005 | Harms et al. | |
| 2005/0262911 A1 | 12/2005 | Dankowicz et al. | |
| 2005/0288672 A1 | 12/2005 | Ferree | |
| 2006/0036323 A1 | 2/2006 | Carl et al. | |
| 2006/0058792 A1 | 3/2006 | Hynes | |
| 2006/0084986 A1 | 4/2006 | Grinberg et al. | |
| 2006/0095044 A1 | 5/2006 | Grady, Jr. et al. | |
| 2006/0149375 A1 | 7/2006 | Yuan et al. | |
| 2006/0241385 A1 | 10/2006 | Dietz | |
| 2006/0247642 A1* | 11/2006 | Stone | A61B 17/0642 623/13.14 |
| 2006/0264935 A1 | 11/2006 | White | |
| 2007/0088359 A1 | 4/2007 | Woods et al. | |
| 2007/0093813 A1 | 4/2007 | Callahan, II et al. | |
| 2007/0093832 A1 | 4/2007 | Abdelgany | |
| 2007/0100341 A1 | 5/2007 | Reglos et al. | |
| 2007/0161985 A1* | 7/2007 | Demakas | A61B 17/7032 606/274 |
| 2007/0198014 A1 | 8/2007 | Graf et al. | |
| 2007/0227216 A1 | 10/2007 | Schalliol | |
| 2007/0233123 A1* | 10/2007 | Ahmad | A61B 17/863 606/307 |
| 2007/0270858 A1* | 11/2007 | Trieu | A61B 17/7098 606/279 |
| 2007/0288011 A1 | 12/2007 | Logan | |
| 2007/0288030 A1 | 12/2007 | Metzger et al. | |
| 2008/0039846 A1* | 2/2008 | Lee | A61B 17/686 606/63 |
| 2008/0086127 A1 | 4/2008 | Patterson et al. | |
| 2008/0114370 A1 | 5/2008 | Shoenefeld | |
| 2008/0161815 A1 | 7/2008 | Shoenefeld et al. | |
| 2008/0183214 A1 | 7/2008 | Copp et al. | |
| 2008/0255564 A1 | 10/2008 | Michelson | |
| 2008/0257363 A1 | 10/2008 | Schoenefeld et al. | |
| 2008/0275452 A1 | 11/2008 | Lang et al. | |
| 2008/0306552 A1 | 12/2008 | Winslow | |
| 2008/0312659 A1 | 12/2008 | Metzger et al. | |
| 2008/0319491 A1 | 12/2008 | Schoenefeld | |
| 2009/0076555 A1 | 3/2009 | Lowry et al. | |
| 2009/0087276 A1 | 4/2009 | Rose | |
| 2009/0088674 A1 | 4/2009 | Caillouette et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0105760 A1 | 4/2009 | Frey | |
| 2009/0110498 A1 | 4/2009 | Park | |
| 2009/0138020 A1 | 5/2009 | Park et al. | |
| 2009/0187194 A1 | 7/2009 | Hamada | |
| 2009/0198277 A1 | 8/2009 | Gordon et al. | |
| 2009/0254093 A1 | 10/2009 | White et al. | |
| 2009/0270868 A1 | 10/2009 | Park et al. | |
| 2009/0318981 A1* | 12/2009 | Kang | A61B 17/7098 606/329 |
| 2009/0326537 A1 | 12/2009 | Anderson | |
| 2010/0016984 A1 | 1/2010 | Trabish | |
| 2010/0049195 A1 | 2/2010 | Park et al. | |
| 2010/0082035 A1 | 4/2010 | Keefer | |
| 2010/0087829 A1 | 4/2010 | Metzger et al. | |
| 2010/0100135 A1* | 4/2010 | Phan | A61B 17/7064 606/301 |
| 2010/0100193 A1 | 4/2010 | White | |
| 2010/0106199 A1* | 4/2010 | Sawa | A61B 17/7098 606/304 |
| 2010/0152782 A1 | 6/2010 | Stone et al. | |
| 2010/0191244 A1 | 7/2010 | White et al. | |
| 2010/0217270 A1 | 8/2010 | Polinski et al. | |
| 2010/0217336 A1 | 8/2010 | Crawford et al. | |
| 2010/0298889 A1* | 11/2010 | Wilberg | A61B 17/7098 606/305 |
| 2010/0305700 A1 | 12/2010 | Ben-Arye et al. | |
| 2010/0324692 A1 | 12/2010 | Uthgenannt et al. | |
| 2011/0015636 A1 | 1/2011 | Katrana et al. | |
| 2011/0015639 A1 | 1/2011 | Metzger et al. | |
| 2011/0046735 A1 | 2/2011 | Metzger et al. | |
| 2011/0054478 A1 | 3/2011 | Vanasse et al. | |
| 2011/0060373 A1* | 3/2011 | Russell | A61B 17/0401 606/304 |
| 2011/0071533 A1 | 3/2011 | Metzger et al. | |
| 2011/0093023 A1 | 4/2011 | Lee et al. | |
| 2011/0093086 A1 | 4/2011 | Witt et al. | |
| 2011/0112436 A1* | 5/2011 | Jones | A61B 10/025 600/567 |
| 2011/0137352 A1* | 6/2011 | Biedermann | A61B 17/8635 606/305 |
| 2011/0160736 A1 | 6/2011 | Meridew et al. | |
| 2011/0160867 A1 | 6/2011 | Meridew et al. | |
| 2011/0166578 A1 | 7/2011 | Stone et al. | |
| 2011/0184419 A1 | 7/2011 | Meridew et al. | |
| 2011/0184526 A1 | 7/2011 | White et al. | |
| 2011/0190899 A1 | 8/2011 | Pierce et al. | |
| 2011/0213376 A1 | 9/2011 | Maxson et al. | |
| 2011/0218545 A1 | 9/2011 | Catanzarite et al. | |
| 2011/0224674 A1 | 9/2011 | White et al. | |
| 2011/0288433 A1 | 11/2011 | Kelleher et al. | |
| 2012/0029432 A1* | 2/2012 | Sweeney | A61M 37/00 604/151 |

(56) References Cited

U.S. PATENT DOCUMENTS

| | | | |
|---|---|---|---|
| 2012/0041445 A1 | 2/2012 | Roose et al. | |
| 2012/0130434 A1 | 5/2012 | Stemniski et al. | |
| 2012/0150243 A9 | 6/2012 | Crawford et al. | |
| 2012/0179259 A1 | 7/2012 | McDonough et al. | |
| 2012/0197311 A1* | 8/2012 | Kirschman | A61B 17/7098 606/304 |
| 2012/0215315 A1 | 8/2012 | Hochschuler et al. | |
| 2012/0245587 A1 | 9/2012 | Fang | |
| 2013/0006251 A1 | 1/2013 | Aram et al. | |
| 2013/0053854 A1 | 2/2013 | Schoenefeld et al. | |
| 2013/0110174 A1 | 5/2013 | Marik | |
| 2013/0123850 A1 | 5/2013 | Schoenefeld et al. | |
| 2014/0137618 A1 | 5/2014 | Isaacs | |
| 2014/0379032 A1 | 12/2014 | Hennard | |
| 2015/0047410 A1 | 2/2015 | Petit et al. | |
| 2015/0119939 A1 | 4/2015 | Frey et al. | |
| 2015/0127053 A1 | 5/2015 | Maruenda Paulino et al. | |
| 2015/0297249 A1 | 10/2015 | Catanzarite | |
| 2016/0000489 A1* | 1/2016 | Kaloostian | A61B 17/8685 606/323 |
| 2016/0030067 A1 | 2/2016 | Frey et al. | |
| 2016/0166301 A1* | 6/2016 | Papangelou | A61B 17/8095 606/232 |
| 2016/0270802 A1 | 9/2016 | Fang et al. | |
| 2017/0215857 A1 | 8/2017 | D'Urso | |
| 2018/0042646 A1* | 2/2018 | Frey | A61B 17/8625 |
| 2018/0280061 A1* | 10/2018 | Frey | A61B 17/7032 |
| 2018/0317971 A1* | 11/2018 | Prevost | A61B 17/8605 |
| 2019/0167326 A1* | 6/2019 | Greenhalgh | A61B 17/8625 |
| 2019/0343566 A1* | 11/2019 | Tempco | A61B 17/7059 |
| 2019/0343567 A1* | 11/2019 | Tempco | A61B 17/863 |

FOREIGN PATENT DOCUMENTS

| | | |
|---|---|---|
| CN | 201275138 | 7/2009 |
| CN | 201404283 | 2/2010 |
| CN | 101390773 | 11/2010 |
| CN | 101953713 | 1/2011 |
| CN | 104306061 | 1/2015 |
| CN | 105078563 | 11/2015 |
| CN | 106175911 | 12/2016 |
| CN | 104224306 | 8/2017 |
| DE | 102013110699 | 4/2015 |
| DE | 202014011170 U1 | 4/2018 |
| EP | 2168507 | 3/2010 |
| EP | 2957244 | 12/2015 |
| EP | 2749235 | 8/2017 |
| EP | 3381382 | 10/2018 |
| FR | 3012030 | 12/2015 |
| FR | 3023655 | 4/2018 |
| GB | 2447702 | 9/2008 |
| JP | 10071157 | 3/1998 |
| JP | 2002531214 | 9/2002 |
| JP | 2005118569 | 5/2005 |
| JP | 2006528533 | 12/2006 |
| JP | 2007502692 | 2/2007 |
| JP | 2007510482 | 4/2007 |
| JP | 2012143379 | 8/2012 |
| JP | D1508406 | 10/2014 |
| WO | WO2004071314 | 8/2004 |
| WO | 200503710 | 4/2005 |
| WO | 2006039266 | 4/2006 |
| WO | 2006066053 | 6/2006 |
| WO | 2006079531 | 8/2006 |
| WO | 2007037920 | 4/2007 |
| WO | 2007145937 | 12/2007 |
| WO | 2008027549 | 3/2008 |
| WO | WO2009004625 | 1/2009 |
| WO | 2009035358 | 3/2009 |
| WO | WO2006017641 | 4/2009 |
| WO | WO2008157412 | 4/2009 |
| WO | 2009129063 | 10/2009 |
| WO | 2009105106 | 12/2009 |
| WO | WO2010033431 | 3/2010 |
| WO | 2010148103 | 12/2010 |
| WO | 2011041398 | 4/2011 |
| WO | 2011080260 | 7/2011 |
| WO | 2011106711 | 9/2011 |
| WO | 2011109260 | 9/2011 |
| WO | WO2012082164 | 6/2012 |
| WO | 2012152900 | 11/2012 |
| WO | 2013041618 | 3/2013 |
| WO | WO2013041618 | 3/2013 |
| WO | 2013104682 | 7/2013 |
| WO | WO2013169674 | 11/2013 |
| WO | WO2013173700 | 11/2013 |
| WO | WO2014070889 | 5/2014 |
| WO | 2014088801 | 6/2014 |
| WO | WO2014090908 | 6/2014 |
| WO | WO2014095853 | 6/2014 |
| WO | 2014143762 | 9/2014 |
| WO | WO2014198279 | 12/2014 |
| WO | WO2016148675 | 9/2016 |

OTHER PUBLICATIONS

Juvinall et al. "Fundamentals of Machine Component Design," Wiley, Dec. 2004, 4th edition, 5 pages [retrieved from: http://tocs.ulb.tu-darmstadt.de/178455539.pdf].

International Search Report and Written Opinion for International (PCT) Patent Application No. PCT/US08/08637 dated Oct. 20, 2009, 8 pages.

International Preliminary Report on Patentability for International (PCT) Patent Application No. PCT/US08/08637 dated Jan. 19, 2010, 6 pages.

Official Office Action for Australian Patent Application No. 52008276577 Dated Nov. 2, 2012 5 pages.

Notice of Acceptance for Australia Patent Application No. 2008276577, dated Jan. 21, 2014 2 pages.

Official Action for Australia Patent Application No. 2014202363, dated Nov. 14, 2014 6 pages.

Official Action for Australia Patent Application No. 2014202363, dated Apr. 1, 2015 3 pages.

Official Action for Australia Patent Application No. 2014202363, dated Aug. 3, 2015 4 pages.

Official Action for Australia Patent Application No. 2014202363, dated Sep. 18, 2015 6 pages.

Official Action for Canada Patent Application No. 2,693,682, dated Jan. 21, 2014 2 pages.

Extended European Search Report for European Patent Application No. 08794499.7 dated Oct. 8, 2012, 13 pages.

Official Action for European Patent Application No. 08794499.7, dated Jul. 2, 2013 3 pages.

Notice of Allowance for European Patent Application No. 08794499.7 dated Mar. 19, 2014 6 pages.

Extended Seach Report for European Patent Application No. 14180580.4, dated Oct. 15, 2015 9 pages.

Official Action (with English Translation) for Japanese Patent Application No. 2010-517004 dated Jan. 15, 2013 6 pages.

Official Action (with English Translation) for Japanese Patent Applicaiton No. 2010-517004 dated Oct. 11, 2013 4 pages.

Re-Examination Report with English Translation for Japan Patent Application No. 2010-517004, dated Apr. 1, 2014 2 pages.

Official Action with English Translation for Japan Patent Application No. 2010-517004, dated Dec. 5, 2014 4 pages.

Official Action for U.S. Appl. No. 12/172,996, dated Apr. 13, 2011 5 pages Restriction Requirement.

Official Action for U.S. Appl. No. 12/172,996, dated Jun. 9, 2011 10 pages.

Official Action for U.S. Appl. No. 12/172,996, dated Dec. 7, 2011 10 pages.

Official Action for U.S. Appl. No. 12/172,996, dated Sep. 25, 2014 11 pages.

Official Action for U.S. Appl. No. 12/172,996, dated May 21, 2015 11 pages.

Official Action for U.S. Appl. No. 14/478,744, dated Jul. 30, 3015 8 pages.

(56) References Cited

OTHER PUBLICATIONS

"Introducing IntelliSense Drill Technology®", McGinley Orthopaedic Innovations, 1 page, [captured Feb. 29, 2016 from: http://web.archive.org/web/20160229042028/http://www.mcginleyorthopaedicinnovations.come/index.php?/drill].
Brussel et al. "Medical Image-Based Design of an Individualized Surgical Guide for Pedicle Screw Insertion." 18th Annual International Conference of the IEEE Engineering in Medicine and Biology Society, Amsterdam 1996, pp. 225-226.
Dai et al. "Surgical treatment of the Osteoporotic spine with bone cement-injectable cannulated pedicle screw fixation: technical description and preliminary application in 43 patients, " Clinics, Feb. 2015, vol. 70, No. 2, pp. 114-119.
Hong et al. "Binder jetting 3D printing and alloy development of new biodegradable Fe—Mn—Ca/Mg alloys," Acta Thomaterialia, Nov. 2016, vol. 45, pp. 375-386 (Abstract Only) 4 pages.
Jakus et al. "Hyperelastic "bone": A highly versatile, growth factor-free, osteoregenerative, scalable, and surgically friendly biomaterial," Science Translational Medicine, Sep. 2016, vol. 8, No. 358, pp. 358ra127 (Abstract only) 5 pages.
Lu et al. "A novel computer-assisted drill guide template for lumbar pedicle screw placement: a cadaveric and clinical study." The International Journal of Medical Robotics and Computer Assisted Surgery, Jun. 2009, vol. 5, No. 2, pp. 184-191. (Abstract only).
Lu et al. "A Noverl Patient-Specific Navigational Template for Cervical Pedicle Screw Placement," Spine, Dec. 15, 2009, vol. 34, No. 26, pp. E959-E966 (Abstract only).
Owen et al. "Rapid prototype patient-specific drill template for cervical pedicle screw placement." Computer Aided Surgery, Sep. 2007, vol. 12, No. 5, pp. 303-308 (Abstract Only).
Ryken et al. "Image-based drill templates for cervical pedicle screw placement Laboratory investigation," Journal of Neurosurgery, Jan. 2009, vol. 10, No. 1 (Abstract Only).
Yin et al. "Computer aid designed digital targeting template of pedicle of vertebral arch for atlantoaxial nailing," IT in Medicine & Education, 2009. ITIME '09. Aug. 14-16, 2009, vol. 1 (Abstract Only).
International Search Report and Written Opinion for International (PCT) Patent Application No. PCT/US11/42412 dated Nov. 8, 2011, 8 pages.
International Preliminary Report on Patentability for international (PCT) Patent Application No. PCT/US11/42412 dated Jan. 17, 2013, 7 pages.
Official Action for Australian Patent Application No. 2011276468 dated Apr. 10, 2013 3 pages.
Official Action for Canada Patent Application No. 2,802,094, dated Feb. 14, 2017, 4 pages.
Partial Search Report for European Patent Application No. 11804191.2, dated Jan. 20, 2015, 6 pages.
Extended Search Report for European Patent Application No. 11804191.2 dated May 7, 2015 8 pages.
Official Action for European Patent Application No. 11804191.2, dated Feb. 17, 2017 5 pages.
Official Action with English Translation for Japan Patent Application No. 2013-518663, dated May 12, 2015 4 pages.
Notice of Allowance with English Translation for Japan Patent Application No. 2013-518663 dated Dec. 8, 2015 4 pages.
International Search Report and Written Opinion for International (PCT) Patent Application No. PCT/US2013/036535, dated Jun. 26, 2013, 8 pages.
International Preliminary Report on Patentability for International (PCT) Patent Application No. PCT/US2013/036535, ated Oct. 30, 2014, 7 pages.
Official Action with English Translation for China Patent Application No. 201380030638.3, dated May 25, 2016 11 pages.
Official Action with English Translation for China Patent Application No. 201380030638.3, dated Feb. 4, 2017 6 pages.
Extended Search Report for European Patent Application No. 13778164.7, dated Feb. 17, 2016 10 pages.
Notice of Allowance with English Translation for Japan Patent Application No. 2015-207078, dated Jan. 10, 2017 4 pages.
Official Action with English Translation for Russia Patent Application No. 2014143528/14, dated Jan. 13, 2017 8 pages.
International Search Report and Written Opinion for International (PCT) Patent Application No. PCT/US15/32356, dated Oct. 28, 2015 10 pages.
International Preliminary Report on Patentability for International (PCT) Patent Application No. PCT/US2015/032356, dated Dec. 15, 2016 7 pages.
International Search Report and Written Opinion for International (PCT) Patent Application No. PCT/US2016/056970, dated 10, 2017 13 pages.
International Search Report and Written Opinion for International (PCT) Patent Application No. PCT/US2014/041379, dated Oct. 28, 2014, 7 pages.
International Preliminary Report on Patentability for International (PCT) Patent Application No. PCT/US2014/041379, dated Dec. 17, 2015 6 pages.
Official Action for Canada Patent Application No. 2,914,005, dated Feb. 3, 2017 3 pages.
Official Action for U.S. Appl. No. 13/172,683, dated Sep. 10, 2013 7 pages.
Office Action for U.S. Appl. No. 13/172,683, dated Feb. 24, 2014 10 pages.
Notice of Allowance for U.S. Appl. No. 13/172,683, dated Apr. 23, 2014 7 pages.
Notice of Allowance for U.S. Appl. No. 29/409,734, dated May 11, 2012 3 pages.
Notice of Allowance for U.S. Appl. No. 29/427,918, dated Oct. 15, 2012 9 pages.
Notice of Allowance for U.S. Appl. No. 19/432,668 dated Nov. 27, 2013 11 pages.
Notice of Allowance for U.S. Appl. No. 29/476,709, dated Nov. 6 2015, 8 pages.
Notice of Allowance for U.S. Appl. No. 29/476,705, dated Oct. 7, 2015, 8 Pages.
Notice of Allowance for U.S. Appl. No. 29/476,699, dated Oct. 2, 2015, 8 pages.
Notice of Allowance for U.S. Appl. No. 29/496,231, dated Jul. 23, 2015 10 pages.
Notice of Allowance for U.S. Appl. No. 29/538,633, dated Jan. 6, 2016 10 pages.
Official Action for U.S. Appl. No. 13/841,069, dated Jul. 31, 2014 9 pages.
Notice of Allowance for U.S. Appl. No. 13/841,069, dated Sep. 18, 2014 7 pages.
Office Action for U.S. Appl. No. 14/298,634, dated Apr. 27, 2015, 8 pages.
Office Action for U.S. Appl. No. 14/298,634, dated Jul. 7, 2015 6 pages.
Notice of Allowance for U.S. Appl. No. 14/298,624, dated Oct. 7, 2015 7 pages.
Notice of Allowance for U.S. Appl. No. 14/883,299, dated Mar. 20, 2017 12 pages.

* cited by examiner

FIXATION DEVICES HAVING FENESTRATIONS AND METHODS FOR USING THE SAME

CROSS-REFERENCE TO RELATED APPLICATIONS

This application is a continuation-in-part of U.S. patent application Ser. No. 15/416,975, filed on Jan. 26, 2017. This application also claims priority under 35 U.S.C. § 119(e) to U.S. Provisional Application No. 62/373,855, filed Aug. 11, 2016.

FIELD OF THE INVENTION

The present disclosure relates to the field of medical devices generally. More specifically, the present disclosure relates to a fixation device, such as a screw, comprising one or more fenestrations. Systems and methods for using the foregoing devices are also disclosed herein.

BACKGROUND OF THE INVENTION

Individuals who suffer degenerative disc disease, natural spine deformations, a herniated disc, spine injuries or other spine disorders often require surgery on the affected region to relieve pain and prevent further injury. Such spinal surgeries may involve fixation of two or more adjacent vertebral bodies. For patients with varying degrees of degenerative disc disease and/or nerve compression with associated lower back pain, spinal fusion surgery or lumbar arthrodesis ("fusion") is commonly used to treat the degenerative disease. Fusion commonly involves distracting and/or decompressing one or more intervertebral spaces, followed by removing any associated facet joints or discs, and then joining or "fusing" two or more adjacent vertebra together. Fusion of vertebral bodies also commonly involves fixation of two or more adjacent vertebrae, which may be accomplished through introduction of rods or plates, and screws or other devices into a vertebral joint to join various portions of a vertebra to a corresponding portion on an adjacent vertebra. Given the complexities of surgical procedures, as well as anatomical variation between patients who receive surgical devices, it is often challenging to provide a device or implant that achieves the needs of a particular patient without completely customizing the device or implant for a single patient.

Many prior art fixation devices suffer from significant disadvantages, such as poor stability, poor flexibility, poor accuracy, difficulty in handling, lack of customized features, inability to combine with other materials, loss of fixation over time, subsidence and other disadvantages. Certain fixation devices also impair visibility and provide little or no ability for the operator to gauge depth or accuracy. These problems and shortcomings are even more noticeable for fixation devices used in surgical settings or which otherwise require precision.

In addition, fixation devices used in surgical settings can also suffer from further shortcomings. For example, pedicle screws are subject to relatively high failure rates, which is often attributed to a failure of the bone-screw interface. Screws for use in surgical settings may also be limited for use in only certain bony anatomies, or with only certain types of drilling apparatus, and may not be suitable for combination with other devices or materials.

Accordingly, there is a need for a fixation device that decreases the mean time for affixing the device to the desired location, enhances depth control, stability and accuracy, and which otherwise overcomes the disadvantages of the prior art. There is also need for a more customized fixation device, such as an orthopedic screw, which includes one or more porous elements or fenestrations to aid in osteo-integration when implanting the fixation device. The fixation device may be additively manufactured using biocompatible materials such that the solid and porous aspects of the device are fused together into a single solid construct, and potentially having the porous elements interdigitated within and around various solid elements of the device.

The prior art also fails to teach a system for creating a customized fixation device based on patient data, such as data derived from a patient's MRI or CT scan. For example, the availability of patient-specific data (for example, a vertebral body) may allow a surgeon to accommodate for subtle variations in the position and orientation of a screw or other fixation device to avoid particular bony anatomy, or irregularities in the positioning and alignment of the adjoining vertebral bodies. As another example, the use of patient data may also assist a surgeon in selecting a desired trajectory for an fixation device so as to avoid, for example, crossing the pedicle wall and violating the spinal canal during a spine-related procedure. The use of patient-specific data permits the surgeon to avoid these types of mistakes and may comprise specific orientation, end-stops/hard stops, or other safety related features to avoid over-torque or over-insertion of the fixation device. This data also permits the surgeon to quickly and efficiently locate and place devices with corresponding patient-contacting surface(s), while ensuring the fixation device is in the appropriate location and orientation.

It would therefore be advantageous to provide a fixation device that significantly reduces, if not eliminates, the shortcoming, problems and risks noted above. Other advantages over the prior art will become known upon review of the Summary and Detailed Description and the appended claims.

BRIEF SUMMARY OF THE INVENTION

According to various embodiments presented herein, the present disclosure describes a fixation device, such as a screw, comprising one or more fenestrations which permit introduction of at least one other material or substance to through the fenestrations in the fixation device. In other embodiments, the fenestrations permit the fixation device to capture and retain material. In yet another aspect of the present disclosure, a method of using the fixation devices described herein is disclosed, including but not limited to in a surgical setting.

One particular aspect of the present disclosure involves a fixation device, such as an orthopedic pedicle screw or implant, that is manufactured such that it includes one or more porous elements or fenestrations in order to aid in osteo-integration of the implanted fixation device. For instance, a pedicle screw (as one type of fixation device) may be additively manufactured using biocompatible materials such that the solid and porous aspects of the screw are fused together into a single solid construct with the porous elements interdigitated within and around various solid elements of the screw.

In yet another aspect, a surgical screw design having at least a portion or section incorporating a porous structure enables bony ingrowth through the porous section/portion of the screw, and thereby facilitate biocompatibility and improve mechanical characteristics. The porous elements of the screw may be designed to more closely resemble that of the patient's anatomy, in order to reduce discontinuities and stress risers at the bone/screw interface. Bony ingrowth within one or more porous elements of the screw in turn facilitates screw pullout strength, and may reduce the risk of loosening of a fixation device under dynamic loading situations.

Incorporated by reference in their entireties are the following U.S. patents and patent applications directed generally to methods and apparatus related to surgical procedures, thus providing written description support for various aspects of the present disclosure. The U.S. patents and pending applications incorporated by reference are as follows: U.S. Pat. Nos. 7,957,824, 7,844,356, 7,658,610, 6,830, 570, 6,368,325, 3,486,505 and U.S. Pat. Pub. Nos. 2010/0217336, 2009/0138020, 2009/0087276, 2008/0161817, 2008/0114370, and 2007/0270875.

Additionally, U.S. Pat. Nos. 8,758,357, 8,870,889, 9,198,678 and 9,642,633 are incorporated by reference for the express purpose of illustrating systems and methods for creating a device, such as the one described herein, using additive manufacturing or other techniques, wherein the device incorporates one or more patient-matched surfaces or is otherwise customized to a particular patient.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel apparatus described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

The Summary is neither intended, nor should it be construed, as being representative of the full extent and scope of the present disclosure. Moreover, references made herein to "the present disclosure" or aspects thereof should be understood to mean certain embodiments of the present disclosure, and should not necessarily be construed as limiting all embodiments to a particular description. The present disclosure is set forth in various levels of detail in the Summary as well as in the attached drawings and the Detailed Description, and no limitation as to the scope of the present disclosure is intended by either the inclusion or non-inclusion of elements or components when describing certain embodiments herein. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

The accompanying drawings, which are incorporated herein and constitute a part of the specification, illustrate embodiments of the disclosure, and together with the Summary and the Detailed Description serve to explain the principles of these embodiments. In certain instances, details that are not necessary for an understanding of the disclosure or that render other details difficult to perceive may have been omitted. It should be understood, of course, that the present disclosure is not necessarily limited to the particular embodiments illustrated herein. Additionally, it should be understood that the drawings are not necessarily to scale. In the drawings.

Similar components and/or features may have the same reference number. Components of the same type may be distinguished by a letter following the reference number. If only the reference number is used, the description is applicable to any one of the similar components having the same reference number.

DETAILED DESCRIPTION OF THE INVENTION

The present disclosure has significant benefits across a broad spectrum of endeavors. It is the Applicant's intent that this specification and the claims appended hereto be accorded a breadth in keeping with the scope and spirit of the disclosure and various embodiments disclosed, despite what might appear to be limiting language imposed by specific examples disclosed in the specifications. To acquaint persons skilled in the pertinent arts most closely related to the present disclosure, preferred and/or exemplary embodiments are described in detail without attempting to describe all of the various forms and modifications in which the novel apparatus, devices, systems and methods might be embodied. As such, the embodiments described herein are illustrative, and as will become apparent to those skilled in the arts, may be modified in numerous ways within the spirit of the disclosure.

By way of providing additional background, context, and to further satisfy the written description requirements of 35 U.S.C. § 112, the following are incorporated by reference in their entireties for the express purpose of explaining and further describing the various tools and other apparatus commonly associated therewith surgical procedures, including minimally invasive surgery ("MIS") procedures: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; and U.S. Pat. Appl. No. 2008/0255564 to Michelson.

Referring now to FIGS. 1-9, varying embodiments of the present disclosure are shown. The fixation devices shown in FIGS. 1-9 preferably comprise a porous or fenestrated structure, which may be exposed at specific regions along the fixation device, and which aid with osteo-integration while increasing the mechanical stability of the device. Various benefits of the fixation device, which in a preferred embodiment is in the form of a screw, are described herein.

Figure 1:
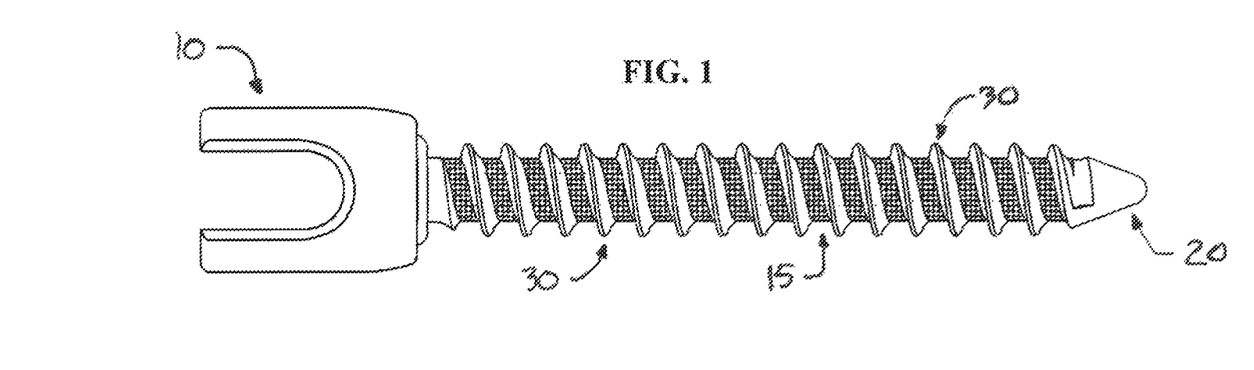
FIG. 1 shows a side elevation view of a fixation device according to one embodiment of the present disclosure.

In the embodiment of FIG. 1, the fixation device is provided in the form of a screw having a head portion 10 and a distal portion 20, with threads 30 located on the shaft 15 between the head portion 10 and the distal portion 20. In certain embodiments, the head portion 10 is affixed to the body of the fixation device, while in other embodiments the head is allowed to float and thereby provide a poly-axial screw assembly. In other embodiments, the head may be temporarily attached to the body of the fixation device. According to this particular embodiment, the porous or fenestrated structure is comprised of the shaft 15 of the screw, but not covering the head portion 10 or the threads 30. The number of fenestrations or porosity of the porous structure of the screw may be greater or lesser than depicted in FIG. 1.

Figure 2:
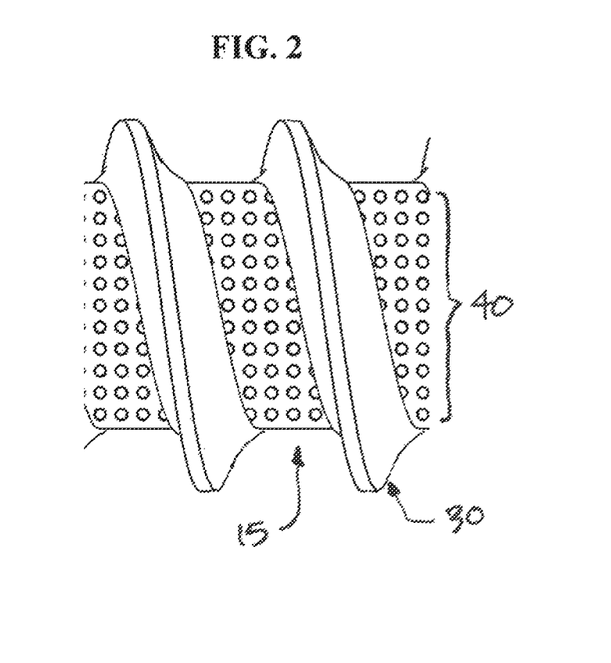
FIG. 2 shows a detailed view of the fixation device of FIG. 1.

Referring now to FIG. 2, a detailed view of the porous screw is depicted. In this drawing, the fenestrations 40 are arranged in series and extend substantially the entire width of the shaft 15 between the threads 30. In alternate embodiments, the fenestrations may be fewer in number than shown, and may not be uniform in their location and arrangement. The fenestrations may be circular or any other shape suitable for the fixation device. In alternate embodiments, the fenestrations extend even through the threads 30 of the screw.

The screw may be additively manufactured such that the porous structure may be exposed to the interfacing bone but also contained within the core of the screw. The screw may be additively manufactured, by way of example but not limitation, out of biocompatible alloys, including by using electron-beam melting or selective laser sintering methods to produce various surface finishes on the porous and solid aspects of the screw. The screw may be a manufactured as a single part, fixed angle screw, or may be poly-axial.

Figure 3:
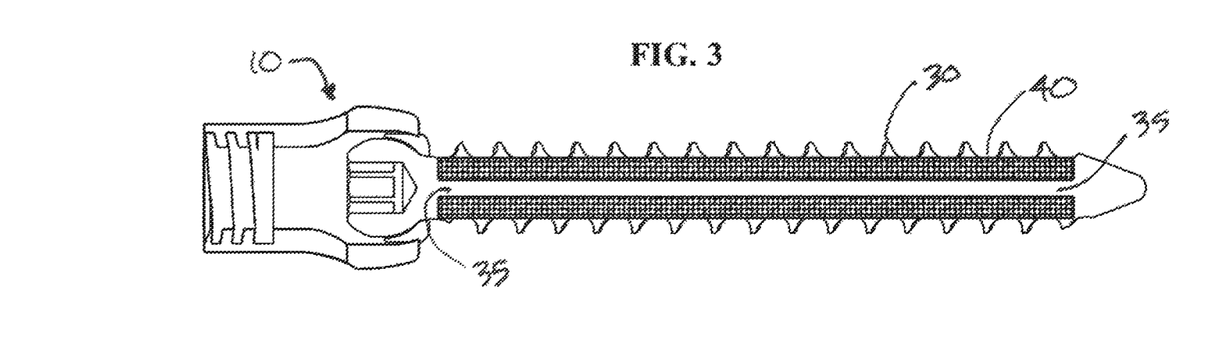
FIG. 3 shows a sectional view of a fixation device according to another embodiment of the present disclosure.
Figure 4:
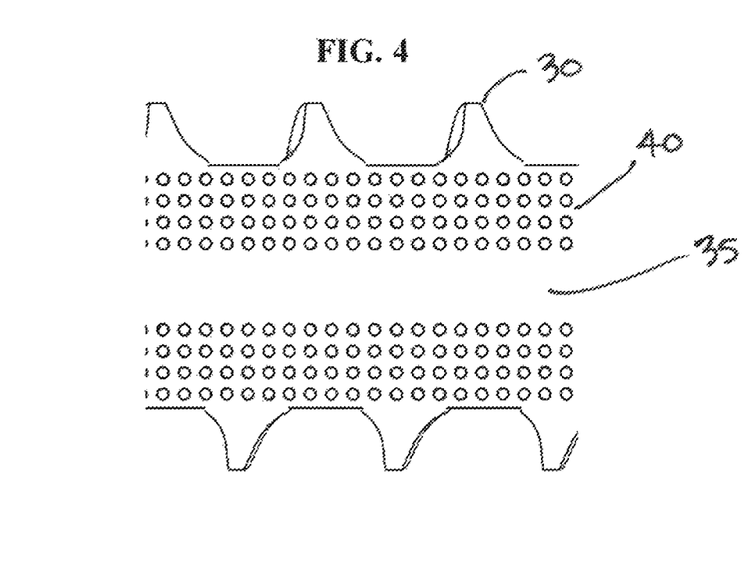
FIG. 4 shows a detailed view of the fixation device of FIG. 3.

Referring now to FIGS. 3-4, the screw may comprise a substantially hollow section that is in communication with the plurality of fenestrations 40. For example, as shown in FIG. 3, the screw may comprise a porous structure in a solid core to provide superior mechanical characteristics. The porous structure may be confined to only a certain region of the screw, or may extend substantially the entire length of the screw.

Figure 5:
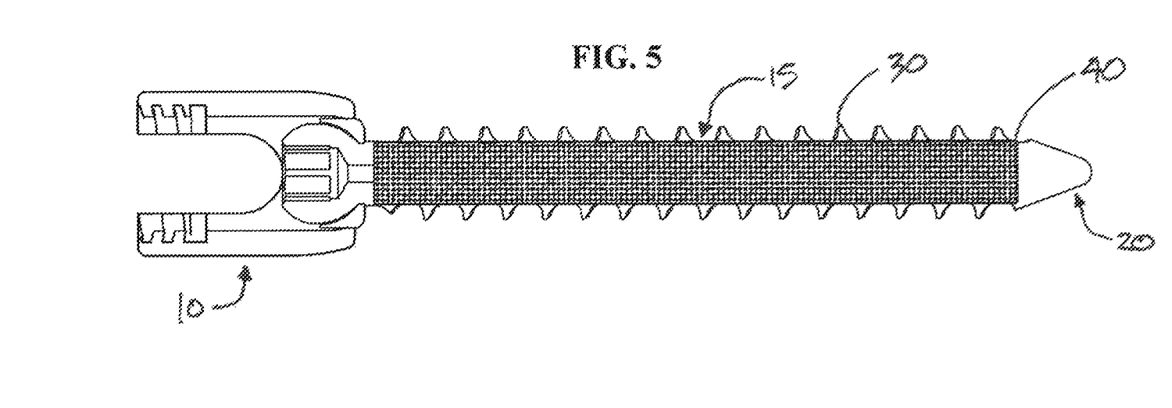
FIG. 5 shows a sectional view of a fixation device according to another embodiment of the present disclosure.

Referring now to FIG. 5, the fenestrations 40 may extend the entire width of the screw for substantially the entire length of the shaft 15, as shown. In this manner, the number of fenestrations 40 may be increased, thereby increasing the number of locations along the outer surface of the screw that either material can be introduced (via the screw) or material may be collected (via suction as described above). In embodiments, the screw may have a longitudinal channel 35 that runs lengthwise through the screw and permits material to be introduced through the longitudinal channel and into the plurality of fenestrations 40. For example, the longitudinal channel may be accessible from the head portion 10 of the screw, such that an operator may inject fluid or solid material into the longitudinal channel 35 and ultimately through the porous structure of the screw via fenestrations 40. In a similar manner, the fenestrations 40 (which surround the outer surface of the shaft 15 of the screw) may be used with vacuum or suction applied to the head portion 10 of the screw to retract material adjacent to the fenestrations 40 and either retained by the porous structure of the screw or within the longitudinal channel 35. By way of example, the screw could either be infused with bone morphogenetic protein or equivalent to enhance fusion between the screw and the patient's anatomy, or the screw could suction and retain autogenous blood into the fenestrations, which in turn stimulates bony ingrowth in the porous section of the screw. Variations on this embodiment are considered within the scope of the present disclosure.

Figure 6:
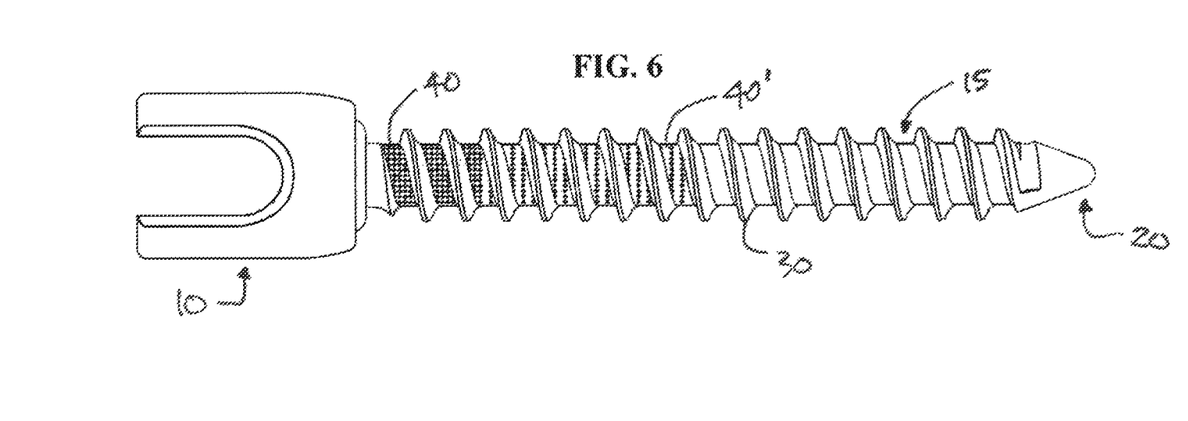
FIG. 6 shows an elevation view of a fixation device according to another embodiment of the present disclosure.
Figure 7:
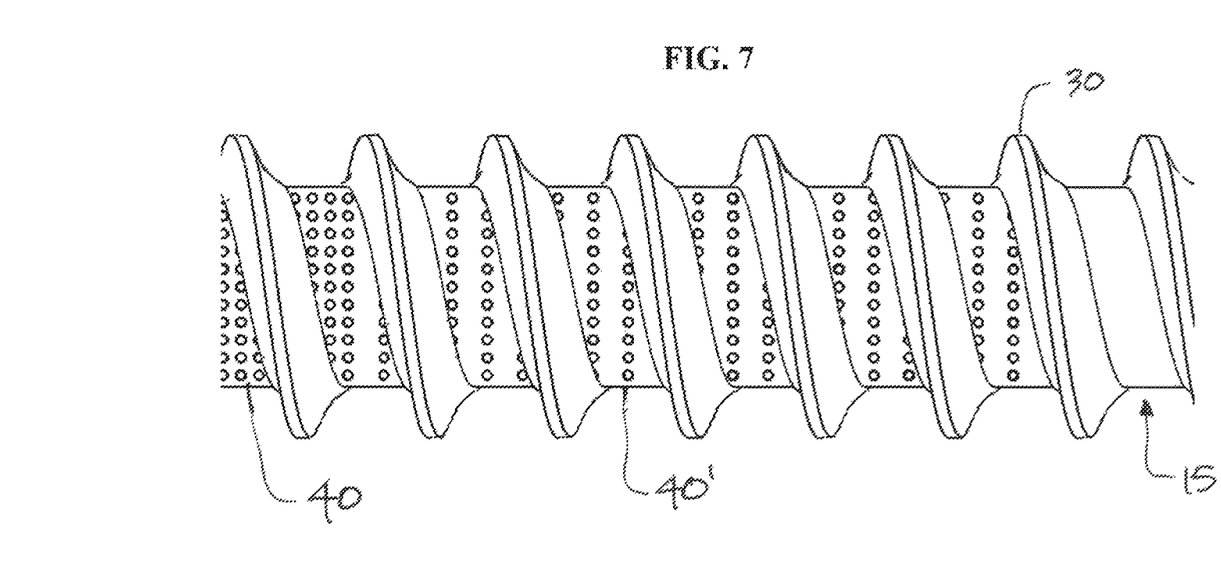
FIG. 7 shows a detailed view of the fixation device of FIG. 6.
Figure 8:
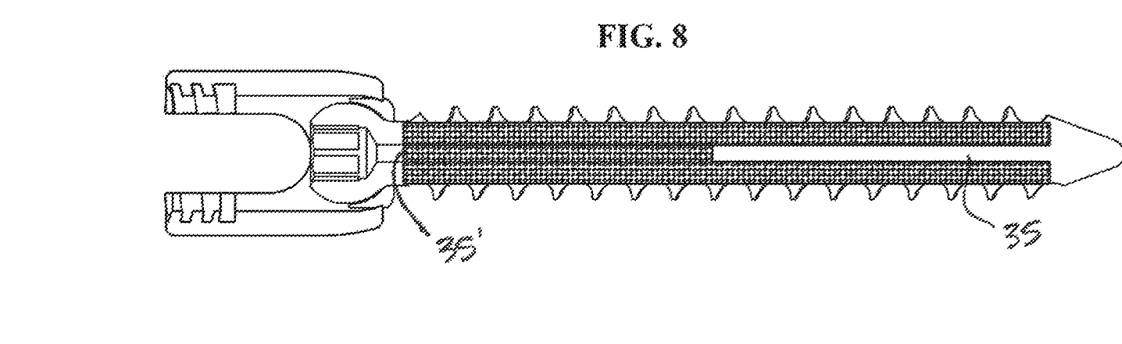
FIG. 8 shows a sectional view of a fixation device according to another embodiment of the present disclosure.
Figure 9:
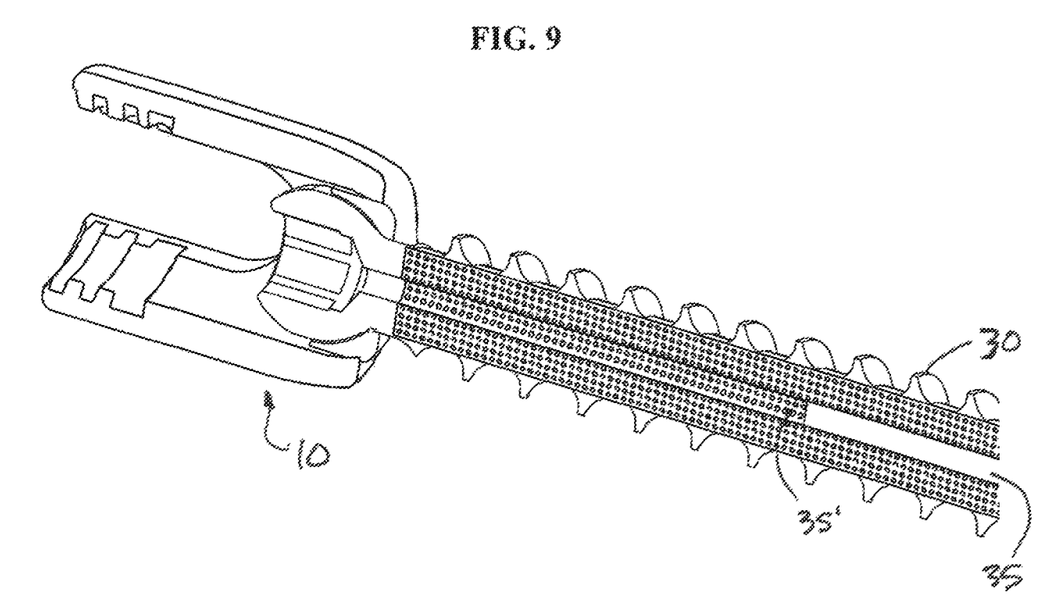
FIG. 9 shows a perspective, sectional view of the fixation device of FIG. 8.

Referring to FIG. 6, one embodiment comprises a varying array of fenestrations 40, which may increase or decrease along the length of the screw. As shown in FIG. 6, the number of fenestrations 40 may vary in a second portion of the screw, such that there is a decreased number or pattern of fenestrations 40' than at a different portion of the screw. In other portions of the screw, the shaft 15 may not comprise any fenestrations at all. This variation is best shown in the detailed view of FIG. 7. In this manner, material may either be collected or introduced via the screw only at desired locations along the length of the screw, which may be desirable given the particular bone density and surrounding anatomical features of a particular patient. In reference to FIGS. 6 and 7, in certain embodiments the longitudinal channel may comprise additional fenestrations in certain portions to better accommodate a particular patient's anatomy. For instance, a first portion of the longitudinal channel 35 is as depicted in FIG. 3, while a second portion of the longitudinal channel 35' may comprise a greater number of fenestrations and therefore a greater porosity.

Further variations of the embodiments described above are shown in FIGS. 8-9. For example, the fixation device may be a pedicle screw, which may be additively manufactured such that the solid and porous aspects of the screw are fused together into a single solid construct. In other embodiments, the solid and porous structure may be co-extensive with the porous elements interdigitated within and around various solid elements of the screw. Variations on these embodiments are considered within the spirit of the presently claimed invention.

The porous elements of the fixation device, screw or implant may be designed to more closely resemble that of a specific patient's anatomy. Accordingly, one advantage of the present disclosure is to promote bony ingrowth throughout the porous portions or sections of the implant, which in turn reduces the risk of loosening of the device under dynamic loading situations.

In still other embodiments, only a portion of the screw is manufactured with a porous surface. For example, the exposed porous aspects of the screw may be localized along the minor diameter of the thread form. The screw may therefore comprise hollow, porous or solid core elements to allow for varying levels of implant stiffness. These areas may be surrounded by a mostly solid thread form to facilitate smooth implantation and firm seating of the screw. Particular reference is made to FIGS. 3-4 when referring to this embodiment.

As referred to above, the porous elements of the screw may be designed with localized fenestrations, which may be at least partially accessible from the screw head, and thereby facilitate delivery of osteogenic agents such as bone-morphogenetic proteins, HA and or allograph or autograph tissue into the porous portions of the screw. This in turn allows for bony ingrowth and greater pullout resistance, as described above. The exposed porous structure may be located on the proximal portion of the screw, adjacent the screw head, in order to localize ingrowth. Localization of ingrowth may increase mechanical characteristics of the bone screw interface, and subsequently allow for easier implant removal in the case of revision surgery. The localized porous elements may be tapered outward to increase the interference fit of the porous elements with the surrounding anatomy.

The porous features are representative of porous cancellous bone with porosity preferably ranging between 30-80% to allow for ingrowth of osteocytes and supporting vasculature. Stated another way, the porous features, when compared to the solid features of the device, make up about 30-80% of the volume of the device. In a most preferred embodiment, the porosity is about 50%. In certain embodiments, the porous structure may be regular and geometric or irregular in form. In yet other embodiments, the porous density may be homogenous throughout the screw, or may be heterogeneous in order to attain desired stiffness and or improve the structural interface of the solid and porous elements.

The implant length and diameter may be pre-surgically planned to match the anatomical size of the patient's anatomy. The implant porosity and subsequent modulus may be pre-surgically planned to match the bone density of the intended patient. For example, in one embodiment, the surgical devices described above may be matched to an anatomic feature of a patient that has degenerated and needs to be restored. In another embodiment, the surgical device may be necessary to correct structural or physiological deformities present in the patient anatomy, and thereby serve to correct position or alignment of the patient anatomy. Other devices may be patient specific but do not serve a restorative or "structural" function.

The surgical devices described herein may be manufactured via additive manufacturing. In the context of spinal implants, the surgical devices may be used in all approaches (anterior, direct lateral, transforaminal, posterior, posterior lateral, direct lateral posterior, etc). Specific features of the surgical device can address certain surgical objectives, for example restoring lordosis, restoring disc height, restoring sagittal or coronal balance, etc. The fixation and surgical devices described herein may then be fabricated by any method. Fabrication methods may comprise the use of a rapid prototyping machine, a 3D printing machine, a stereolithography (STL) machine, selective laser sintering (SLS) machine, or a fused deposition modeling (FDM) machine, direct metal laser sintering (DMLS), electron beam melting (EBM) machine, or other additive manufacturing machine.

To add further stability to the seating and placement of the fixation devices described herein to the patient anatomy, the outer surfaces of the fixation device may further comprise one or more spikes or teeth or other surface features, which serve to contact and at least partially penetrate or "grip" the patient anatomy to secure the fixation device in place. In one embodiment, the surface features may be made of the same material and may be permanently attached to the fixation device. In another embodiment, the surface features may be comprised of an overlay, and/or may be made of a different material, such as the ones described herein, and may further be selectively inserted onto the fixation device(s) as desired.

One having skill in the art will appreciate that embodiments of the present disclosure may have various sizes. The sizes of the various elements of embodiments of the present disclosure may be sized based on various factors including, for example, the anatomy of the patient, the person or other device operating with or otherwise using the apparatus, the surgical site location, physical features of the devices and instruments used with the apparatus described herein, including, for example, width, length and thickness, and the size of the surgical apparatus.

One having skill in the art will appreciate that embodiments of the present disclosure may be constructed of materials known to provide, or predictably manufactured to provide the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, polyethylene, photo-polymers, resins, particularly fiber-encased resinous materials, rubber, latex, synthetic rubber, synthetic materials, polymers, and natural materials.

One having skill in the art will appreciate that embodiments of the present disclosure may be used in conjunction devices that employ automated or semi-automated manipulation. Various apparatus and implants described herein may be provided to facilitate or control the entry point, angular trajectory, height, and/or head orientation of a screw, for example. This is desirable, particularly with placement of screws in the human body, as it permits a surgeon/user to optimize spinal screw head alignment for subsequent rod insertion across multiple bony landmarks. Additionally, by controlling screw placement, a patient specific rod may be designed and manufactured to either match the pre-planned screw placement, or offer angular corrections in order to optimize curvature of the spine.

The present disclosure may also be advantageous in light of recent improvements in decentralized manufacturing. For example, surgical devices may soon be capable of fabrication in a number of different and convenient settings, including but not limited to an off-site manufacturing location, an on-site manufacturing location, using equipment present in a surgeon's clinic or offices or in a public or private hospital. For example, modules may be fabricated based on a particular patient need and immediately fabricated once the need is identified, and then provided directly to the surgeon.

Additional benefits of the systems and methods described herein include improving device fixation, and/or preventing unwanted contact between devices and patient anatomy (e.g. the patient's spinal cord). The further use of methods described above, including the use of software analytics, may further aid in determining screw placement and orientation to achieve the ideal screw placement and/or rod shape. For example, the use of various apparatus described herein to achieve desired screw placement and orientation in turn provides improved alignment of a secondary device, such as a rod, with the screws heads. This benefit in turn allows the surgeon/user to achieve optimal sagittal and/or coronal alignment, which assists in rod placement and improves correction of the patient's anatomy.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For further illustration, the information and materials supplied with the provisional and non-provisional patent applications from which this application claims priority are expressly made a part of this disclosure and incorporated by reference herein in their entirety.

It is expressly understood that where the term "patient" has been used to describe the various embodiments of the disclosure, the term should not be construed as limiting in any way. For instance, a patient could be either a human patient or an animal patient, and the apparatus and methods described herein apply equally to veterinary science as they would to surgical procedures performed on human anatomy. The apparatus and methods described herein therefore have application beyond surgical procedures used by spinal surgeons, and the concepts may be applied to other types of "patients" and procedures without departing from the spirit of the present disclosure.

The foregoing discussion of the disclosure has been presented for purposes of illustration and description. The foregoing is not intended to limit the disclosure to the form or forms disclosed herein. In the foregoing Detailed Description, for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and/or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device configured for fixation to a particular anatomical feature comprising:
    a proximal portion of the device comprising a head for manipulation of the device by at least one tool or instrument, and a distal portion of the device comprising a tip configured to penetrate a surface of the particular anatomical feature;
    a shaft portion between the proximal portion and the distal portion of the device, the shaft portion comprising at least one thread and further comprising one or more fenestrations along an outer surface thereof;
    one or more spikes or teeth comprised of an overlay associated with the exterior of the shaft and configured to interface with bone associated with a patient-specific anatomical feature;
    an internal channel running substantially the entire length of the shaft portion and accessible from the proximal portion of the device, wherein the internal channel is further accessible by the one or more fenestrations; and
    wherein the device is configured to receive a first material by the proximal portion and through the internal channel, and wherein the first material is distributed through the one or more fenestrations.

2. The device of claim 1 wherein the one or more fenestrations are located along the shaft portion of the device and along the at least one thread.

3. The device of claim 1 wherein the one or more fenestrations are in communication with the internal channel by pathways formed in the device.

4. The device of claim 3 wherein the fenestrations and pathways provide porosity of 30-50 percent in the shaft.

5. The device of claim 3 wherein the fenestrations and pathways provide porosity of 50-80 percent.

6. The device of claim 1 wherein the device is formed by a rapid prototyping machine, a 3D printing machine, a stereolithography (STL) machine, a selective laser sintering (SLS) machine, a fused deposition modeling (FDM) machine, a direct metal laser sintering (DMLS) machine, an electron beam melting (EBM) machine, or an additive manufacturing machine.

7. The device of claim 1 wherein the device is made of a stainless steel, a titanium alloy, an aluminum alloy, a chromium alloy, a metal alloy, a PEEK material, a carbon fiber material, an ABS plastic, a polyurethane, a polyethylene, a photo-polymer, a resin, a fiber-encased resinous material, a rubber, a latex, a synthetic rubber, a synthetic material, a polymer, or a natural material.

8. The device of claim 1, further comprising a bone morphogenetic compound associated with the fenestrations.

9. A fixation device comprising:
    a body;
    the body comprising a proximal portion and a distal portion;

the proximal portion comprising a head configured for mating with at least one instrument or tool;

the distal portion comprising a tip configured to penetrate a surface;

the body further comprising a shaft portion between the proximal portion and the distal portion, the shaft portion comprising at least one thread;

the body further comprising a porous structure, wherein the porous structure is formed in the shaft portion and accessible from the exterior of the fixation device;

the body further comprising one or more spikes or teeth selectively inserted onto the exterior of the shaft; and wherein the porous structure is adapted to receive a material to substantially fill the porous structure with the material.

10. The device of claim 9 wherein the porous structure comprises a plurality of hollow pathways within the body, and wherein the plurality of hollow pathways make up 30-80 percent of the volume of the device.

11. The device of claim 10 wherein the plurality of hollow pathways make up 50 percent of the volume of the device.

12. The device of claim 10 wherein the plurality of hollow pathways are intersecting within the shaft portion of the fixation device.

13. The device of claim 10 wherein the porous structure is formed along the shaft portion and along the at least one thread.

14. The device of claim 13 wherein the porous structure is non-uniform about the length of the shaft.

15. The device of claim 10 wherein the shaft portion is comprised of a first portion having a porous structure and a second portion devoid of a porous structure.

16. The device of claim 10 wherein the device is customized for implanting in a patient-specific anatomical feature.

17. The device of claim 16 wherein the device is customized for implanting using a patient-specific surgical guide.

18. The device of claim 17 wherein a length and a diameter of the body is configured to match the size of the patient-specific anatomical feature.

19. The device of claim 17 wherein porous structure is configured to be determined by a bone density of the patient-specific anatomical feature.

20. The device of claim 9, further comprising a bone morphogenetic compound associated with the porous structure.

\* \* \* \* \*